United States Patent [19]

Fujiwara et al.

[11] Patent Number: 5,808,030
[45] Date of Patent: Sep. 15, 1998

[54] HTFIIIA GENE

[75] Inventors: Tsutomu Fujiwara, Naruto; Satoshi Takeda; Yoshikazu Shimada, both of Tokushima; Kouichi Ozaki, Tokyo; Sadahito Shin, deceased, late of Tokushima-ken, all of Japan, by Sadae Kim, legal representative

[73] Assignee: Otsuka Pharmaceutical Co., Ltd., Tokyo, Japan

[21] Appl. No.: 523,376

[22] Filed: Sep. 5, 1995

[30] Foreign Application Priority Data

Sep. 5, 1994 [JP] Japan ................................. 6-211022

[51] Int. Cl.⁶ .................................................. C07H 21/04
[52] U.S. Cl. .............................................................. 536/23.5
[58] Field of Search ............................................... 536/23.5

[56] References Cited

FOREIGN PATENT DOCUMENTS 0704526  4/1996  European Pat. Off. .

OTHER PUBLICATIONS

Moorefield. Purification and cloning of human transcription factor IIIA and studies of the role of upstream sequences in human 5S gene expression. Thesis Dissertation, UMI Dissertation Services, Ann Arbor, MI. Chapter 3, Apr. 1994.

Moorefield et al, *J. Biol. Chem.*, 269(33):20857–20865 (1994).

Waldschmidt et al, *Eur. J. Biochem.*, 196:167–176 (1990).

Stevens et al, "Gene-based STSs as the Basis for a Human Gene Map", Abstract, Acc. No. T15760 EMBL Database Entry HS760 (1994).

Okubo et al, "Gene Expression of Human Promyelotic Cell Line HL60 Before and After Induction of Differentiation. A New Application of 3' Directed cDNA Sequencing", Abstract, Acc. No. D19678, EMBL Database Entry Hsgs00633 (1994).

Moorefield et al. Purification and characterization of human TFIIIA. Journal of Cellular Biochemistry. Supp. 17A, p. 85. Abstract, Jan. 9, 1993.

Seifart et al. Purification of human transcription facotr IIIA and its interaction with a chemically synthesized gene encoding human 5 S rRNA. The Journal of Biological Chemistry. vol. 264, No. 3, pp. 1702–1709, Jan. 25, 1989.

*Primary Examiner*—Vasu S. Jagannathan
*Assistant Examiner*—Brian K. Lathrop
*Attorney, Agent, or Firm*—Sughrue,Mion,Zinn,Macpeak & Seas, PLLC

[57] ABSTRACT

An isolated hTFIIIA gene having a nucleotide sequence coding for the amino acid sequence of SEQ ID NO:1, as disclosed, and in particular the hTFIIIA gene having the nucleotide sequence of SEQ ID NO:2. The gene can be used to express a corresponding hTFIIIA protein. The gene and protein serve as transcription regulating factors, and are useful in the diagnosis or identification of hereditary disease, such as cancer or other diseases resulting from abnormal transcriptional control and, further, in analyzing the mechanisms of action thereof.

2 Claims, 1 Drawing Sheet

FIG. 1

HTFIIIA GENE

TECHNICAL FIELD

The present invention relates to a gene coding for human transcription factor IIIA (hereinafter referred to as hTFIIIA).

BACKGROUND ART

Since TFIIIA was purified as a transcription factor for the first time in 1980 from Xenopus oocytes [Segall et al., J. Biol. Chem., 255, 11986–11991 (1980)], a number of in vivo and in vitro studies have been made in Xenopus for elucidating the mechanism of transcriptional control by said TFIIIA [e.g. Del et al., Nucleic Acids Res., 19, 6197–6203 (1991); Smith et al., Nucleic Acids Res., 19, 6871–6876 (1991); Liao et al., J. Mol. Biol., 223, 857–871 (1992); Del et al., J. Mol. Biol., 233, 567–579 (1993)].

The above-mentioned Xenopus TFIIIA is necessary for the initiation of 5S RNA gene transcription [Sakonji et al., Cell, 19, 13–25 (1980)] and binds to an internal control region of the 5S gene [Bogenhagen et al., Cell, 19, 27–35 (1980)].

The nucleic acid sequence of the Xenopus TFIIIA cDNA and the corresponding amino acid sequence have already been reported [Ginsberg et al., Cell, 39, 479–489 (1984)]. Said gene codes for nine zinc finger domains (repetitions of the $Cys_2His_2$ ($C_2H_2$) motif), and this structure is regarded as an essential domain for a group of DNA-binding proteins [Miller et al., EMBO J., 4, 1607–1614 (1985)].

It has been established that a yeast gene coding for a protein homologous to the Xenopus TFIIIA also has the same $C_2H_2$ motif [Archambault et al., J. Biol. Chem., 267, 3283–3288 (1992)].

It is further known that, in human, DNA binding transcriptional factors such as the human Wilms tumor gene WT1 [Gessler et al., Nature, 343, 774–778 (1990)], the human transcriptional repressor YY1 [Shi et al., Cell, 67, 377–388 (1991)], the human MYC-associated zinc finger protein maz [Bossone et al., Proc. Natl. Acad. Sci., U.S.A., 89, 7452–7456 (1992)] and sp1 [Kuwahara et al., Biolchem., 29, 8627–8631 (1990)] have finger domains of the above $C_2H_2$ type.

In contrast to Xenopus TFIIIA, little is known about hTFIIIA. Thus, while, in 1989, a hTFIIIA-like protein (35kDa protein) was purified from HeLa cells and its inter-action with the human 5S RNA gene was shown [Seifart et al., J. Biol. Chem., 264, 1702–1709 (1989)], no hTFIIIA-encoding gene has been reported as yet.

Accordingly, it is an object of the present invention to isolate and provide a hTFIIIA gene.

Another object of the present invention is to reveal the nucleic acid sequence of the hTFIIIA gene and the corresponding amino acid sequence and thereby shed light on the human transcriptional mechanism and provide a use thereof.

DISCLOSURE OF THE INVENTION

As a result of their intensive investigations, the present inventors successfully isolated a cDNA coding for hTFIIIA, determined the whole cDNA sequence and the corresponding amino acid sequence, caused its expression in various tissues and revealed its locus on chromosome. Based on the findings thus obtained, the present invention has now been completed.

Thus, the present invention provides a hTFIIIA coding for an amino acid sequence defined by SEQ ID NO:1.

Hereinafter, in the present specification, abbreviations are used for amino acids, peptides, base sequences, nucleic acids and so forth as recommended by IUPAC and IUB and in "Guideline for drafting specifications etc. which contain base sequences and/or amino acid sequences" (edited by Japanese Patent Office) or conventionally used in the relevant field of art.

The hTFIIIA gene of the present invention has an open reading frame comprising 1269 nucleotides (nucleic acids) coding for 423 amino acid residues as shown under SEQ ID NO:1, and is characterized by coding for nine $C_2H_2$ type zinc finger domains. When compared with the Xenopus TFIIIA gene, it shows 63% homology with respect to nucleic acids and 58% homology with respect to amino acids.

The hTFIIIA encoded by the gene of the present invention supposedly plays a biological role as a DNA binding protein, and said gene is useful as a transcription regulating factor. In particular, the gene of the present invention is expressed generally in various tissues, hence presumably plays an important role in the initiation of 5S ribosomal RNA gene transcription and in the maintenance of the stability of transcription of other genes, thus being involved in life-supporting and controlling functions.

In particular, a very large number of diseases accompanying a disorder in transcriptional control have recently become known. For example, many of oncogene products act as transcription regulating factors, and disorders therein lead to canceration of cells. In promyelocytic leukemia, chromosomal translocation results in a disorder in transcriptional control, which in turn causes canceration. High-level expression of the regulatory factor Hox2.4 induces leukemia in mice. Thus, a number of hereditary diseases are now known in which a protein concerned shows no abnormality but the pathologic mechanisms of which involve an abnormality of a gene involved in the transcriptional control required for the expression of the gene for said protein. By investigating these gene abnormalities (DNA diagnosis etc.), it is possible to identify hereditary diseases the pathogenetic analysis of which has not sufficiently advanced. The gene of the present invention is useful in such field. The gene of the present invention is also useful in the treatment of diseases through transcriptional control using an antisense or in analyzing the mechanisms of action thereof.

Furthermore, TFIIIA is involved in the transcriptional control of 5S RNA and, therefore, a disorder in this transcriptional control directly leads to a disorder in the synthesis of the protein concerned. Many hereditary diseases showing an abnormality in the quantity of a protein are presumably caused by such disorder in protein synthesis. Thus, the gene of the present invention is expected to be useful also in throwing light on such diseases.

While the gene of the present invention is represented in terms of a single-stranded DNA sequence, as shown under SEQ ID NO:2, the present invention includes, within the scope thereof, a DNA sequence complementary to such single-stranded DNA sequence and a component comprising both of them as well. The DNA sequence shown under SEQ ID NO:2 and representing the gene of the present invention is an example of the combination of codons coding for respective amino acid residues according to the amino acid sequence shown under SEQ ID NO:1. The gene of the present invention is not limited thereto but, of course, can have any DNA base sequence that comprises some other arbitrary combination of codons for respective amino acid residues without altering the above amino acid sequence. The codon selection can be made in a conventional manner, for example taking into consideration the codon employment frequencies in the host to be used [Nucl. Acids Res., 9, 43–74 (1981)].

The gene of the present invention further includes DNA sequences coding for equivalents to the amino acid sequence mentioned above as modified therefrom by deletion and/or substitution of at least one amino acid or partial amino acid sequence thereof or by addition of at least one amino acid or amino acid sequence and having a biological activity similar to that of hTFIIIA. These equivalents may be produced spontaneously or can be produced by posttranslational modification or further can be produced (by modification, mutation, etc.) by modifying the natural gene (gene of the present invention) using such techniques as site-specific mutagenesis [Kramer, W., et al., Nucl. Acids Res., 12, 9441 (1984); Kramer, W. and Frits, H. J., Methods in Enzymology, 154, 350 (1987); Zoller, M. J. and Smith, M., Methods in Enzymology, 100, 468 (1983); Hirose, Susumu, Seikagaku Jikken Koza (Experiments in Biochemistry), 2nd series, vol. 1, "Idenshi Kenkyu-ho (Methods in Genetic Studies) II". 105], by synthesizing modified DNAs using such chemical synthesis techniques as the phosphotriester method [Letsinger, R. L. and Ogilvie, K. K., J. Am. Chem. Soc., 91, 3350 (1969); Merrifield, R. B., Science, 150, 178 (1968)] and the phosphoamidite method [Beaucage, S. L. and Caruthers, M. H., Tetrahedron Lett., 22, 1859 (1981); McBride, L. J. and Caruthers, M. H., Tetrahedron Lett., 24, 245 (1983)], or by a combination of these.

By utilizing the gene of the present invention, namely inserting it, for example, into a microbial vector and cultivating the thus-transformed microorganism, it is possible to cause expression of hTFIIIA with ease and in large quantities and thereby isolate and provide said protein.

The gene of the present invention can be readily produced based on the sequence information on the gene of the present invention as disclosed herein, using general genetic engineering techniques [e.g. Sambrook, J., Fritsch, E. F., Maniatis, T., Molecular Cloning, 2nd edition, Cold Spring Hrbor Laboratory Press (1989); Seikagaku Jikken Koza, 2nd series, "Idenshi Kenkyu-ho I, II, III", edited by Nippon Seikagaku-Kai; Guide to Molecular Cloning Techniques, Berger, S. L, Kimmel, A. R., Methods in Enzymology, vol. 152], among others.

For example, said gene can be produced by selecting, from among a human cDNA library (prepared in a conventional manner from appropriate origin cells containing a gene coding for hTFIIIA), a desired clone using an appropriate probe or antibody specific to the gene of the present invention [cf. e.g. Sugga, S. V., et al., Proc. Natl. Acad. Sci., U.S.A., 78, 6613 (1981); Young, R. A., et al., Science, 222, 778 (1983)].

As examples of the origin cells to be used in the above procedure, there may be mentioned various cells and tissues, and cultured cells derived therefrom, which allow expression of the hTFIIIA gene. Whole RNA separation from these, mRNA separation and purification, and conversion to (synthesis of) cDNA and cloning of the same and other steps can be performed in the conventional manner. Furthermore, cDNA libraries are commercially available and, in the practice of the present invention, such cDNA libraries, for example various cDNA libraries available from Clontech, can also be used.

Screening of the gene of the present invention from such a cDNA library can be carried out in the conventional manner, as mentioned above. As the method of screening, there may be mentioned, for example, the method comprising the use of an anti-hTFIIIA specific antibody against the protein produced by the cDNA and thus selecting a corresponding cDNA clone by means of Western blotting, the method comprising Southern blotting using a probe selectively binding to the objective DNA sequence, the Northern blotting method, and a combination of these. Generally, a DNA sequence chemically synthesized based on the information on the DNA sequence of the gene of the present invention, for instance, is used here as the probe. Of course, it is also possible to use the gene of the present invention already obtained or a fragment thereof as such a probe.

In obtaining the gene of the present invention, the DNA/RNA amplification method comprising the PCR technique [Saiki, R. K., et al., Science, 230, 1350–1354 (1985)] can also be used successfully. Particularly in cases where a full-length cDNA cannot be obtained from the library, the technique of RACE [Rapid Amplification of cDNA Ends; Jikken Igaku, 12 (6), 35–38 (1994)] can suitably be employed. The primers to be used in employing such PCR technique can appropriately be designed based on the sequence information on the gene of the present invention and can be synthesized by a per se known conventional method.

The amplified DNA/RNA fragment can be isolated and purified in the conventional manner, as mentioned above, for example by gel electrophoresis.

The base sequence of the gene of the present invention or of any of various DNA fragments thereof can be determined in the conventional manner, for example by the dideoxy method [Sanger, F., et al., Proc. Natl. Acad. Sci., U.S.A., 74, 5463–5467 (1977)] or the Maxam-Gilbert method [Maxam, A. M. et al., Methods in Enzymology, 65, 499 (1980)]. Such base sequence determination can also be made with ease using a commercially available sequencing kit or the like.

The whole DNA base sequence of a cDNA thus obtained and named clone OTK7 and serving as an example of the gene of the present invention is as shown under SEQ ID NO:3, and the amino acid sequence of hTFIIIA encoded by said cDNA is as shown under SEQ ID NO:1.

In accordance with the present invention, a method of screening the hTFIIIA gene is provided which comprises using a part of the gene of the present invention as a probe. Here, the probe can be labeled, for example by using a random prime DNA labeling kit (available from Takara Shuzo, Amersham, etc.) which makes use of the random prime DNA labeling technique [Feinberg, A. P., et al., Anal. Biochem., 137 266–267 (1984)], and the objective gene can be screened, for example by the plaque hybridization technique [Benton, W., et al., Science, 196, 383–394 (1977)].

Furthermore, it is possible, starting with the gene of the present invention, to obtain recombinant hTFIIIA species in accordance with general gene recombination techniques [cf. e.g. Science, 224, 1431 (1984); Biochem. Biophys. Res. Comm., 130, 692 (1985); Proc. Natl. Acad. Sci., U.S.A., 80, 5990 (1983)]. More specifically, said hTFIIIA species can be produced by constructing a recombinant DNA which allows expression of the gene of the present invention in host cells, introducing the same into the host cells for transformation and cultivating the thus-obtained transformant.

The host cells to be used may be either eukaryotic or prokaryotic. As the expression vector for vertebrate cells, use may be made of those which possess a promoter generally located upstream of the gene to be expressed, an RNA splicing site, a polyadenylation site and a transcription termination sequence and which may have a replication origin as necessary. As eukaryotic microorganisms, frequent use is generally made of yeasts and, among them, yeasts of the genus Saccharomyces can be used with advantage. As the expression vector for eukaryotic micro-organisms such as yeasts, use may be made of pAM82 having a promoter for the acid phosphatase gene [A. Miyanohara et al., Proc. Natl. Acad. Sci., U.S.A., 80, 1–5 (1983)], for instance. As eukaryotic hosts, general and frequent use is made of *Escherichia coli* and *Bacillus subtilis*. When these are used as hosts in the practice of the present invention, it is desirable to use an expression plasmid constructed by inserting the gene of the present invention into a plasmid vector capable of replicating in said hosts in a manner such that said expression plasmid is provided, upstream of the gene of the present invention, with a promoter and the SD (Shine and Dalgarno) base sequence and further with an initiation codon (e.g. ATG) required for the initiation of protein synthesis so that said gene can be expressed. *Escherichia coli* K12, for instance, is frequently used as the host *Escherichia coli* mentioned above, with frequent use being generally made of pBR322 as the vector. These are, however, not limitative but other various per se known strains and vectors may also be used. Usable as the promoter are, for example, the tryptophan (trp) promoter, lpp promoter, lac promoter, $P_L$ promoter, and the like.

The thus-obtained desired recombinant DNA can be introduced into host cells for transformation thereof by various methods generally employed in the art. The transformant obtained can be cultivated by a conventional method. The cultivation results in production and accumulation of the objective hTFIIIA encoded by the gene of the present invention. The medium to be used in said cultivation can be appropriately selected from among various media in common use according to the host cells employed, and the cultivation can be carried out under conditions suited for the growth of the host cells.

In the above manner, the objective recombinant hTFIIIA protein is produced and accumulated or secreted intracellularly or extracellularly of the transformant cells.

The recombinant hTFIIIA can be isolated and purified by various separation procedures utilizing its physical and/or chemical and/or other properties [cf. "Seikagaku (Biochemistry) Data Book", pages 1175–1259, 1st edition, 1st printing, published Jun. 23, 1980 by Tokyo Kagaku Dozin; Biochemistry, vol. 25, No. 25, 8274–8277 (1986); Eur. J. Biochem., 163, 313–321 (1987)]. Concretely, said procedures include such conventional ones as reconstitution treatment, treatment with a protein precipitant (salting out), centrifugation, osmotic shock procedure, ultrasonication, ultrafiltration, molecular sieve chromatography (gel filtration), adsorption chromatography, ion exchange chromatography, affinity chromatography, high-performance liquid chromatography (HPLC), other chromatographic techniques, dialysis, and combinations of these, among others. In the above manner, the desired recombinant hTFIIIA can be produced on a commercial scale with ease and in high yields.

In accordance with the present invention, a hTFIIIA gene is provided, and hTFIIIA can be produced with ease and in large quantities using said gene. The gene and hTFIIIA of the present invention are useful as transcription regulating factors and are useful, among others, in the diagnosis and identification of cancer and other hereditary diseases resulting from disorders in transcriptional control, in the treatment of such diseases by the transcriptional control, and in analyzing the mechanisms of action of such control.

EXAMPLES

The following examples are further illustrative of the present invention.
Example 1
(1) Cloning and sequencing As a result of sequence analysis of clones arbitrarily selected from a human fetal brain cDNA library, a 1.3 kb clone showing a high level of homology to Xenopus TFIIIA was found and named OTK7-1. Sequence analysis revealed that this clone lacks a 5' portion of the gene.
(2) 5' RACE A cDNA clone containing the 5' portion of the gene was isolated by 5' RACE using a commercial kit (5'-AmpliFINDER™ RACE kit, Clontech).

In that case, three primers corresponding to OTK7-1, namely H11-R (the base sequence shown under SEQ ID NO:4), H11-E (the sequence shown under SEQ ID NO:5) and H11-H (shown under SEQ ID NO:6), and one primer (AP-2; shown under SEQ ID NO:7) complementary to an anchor primer (shown under SEQ ID NO:8) were synthesized.

A 300 ng portion of human brain poly $A^+$ RNA (Clontech) was reverse-transcribed with the primer H-11R for single-stranded cDNA synthesis.

Thus, 9 µl of poly $A^+$ RNA (300 ng/9 µl) and 1 µl of primer H11-R (10 picomoles/µl) were preincubated at 65° C. for 5 minutes, a reaction mixture [9.2 µl of DEPC-treated $H_2O$/9 µl of 4×reverse transcriptase buffer/1.6 µl of RNase inhibitor (40 units/µl)/3.7 µl of dNTPmix (10 mM each nucleotide)/0.5 µl of AMV reverse transcriptase (25 units/µl)] was added, and incubation was performed at 52° C. for 30 minutes. The reaction was terminated by adding 10 µl of 0.5M EDTA, the template poly $A^+$ RNA was then hydrolized by adding 10 µl of 6N NaOH, and the excess primer H11-R was removed using a GENO-BIND™ system. Following precipitation with ethanol, the cDNA pellet was resuspended in 6 µl of $H_2O$.

Then, the single-stranded anchor oligonucleotide (anchor primer) was ligated to the 3' end of the above-mentioned cDNA using T4 DNA ligase, as follows.

A mixture composed of 2.5 µl of the above cDNA, 2 µl of the anchor primer (4 picomoles), 5 µl of 2×ligation buffer and 0.5 µl of T4 DNA ligase (20 units/µl) was incubated at room temperature for 18 hours.

The ligated mixture was 10-fold diluted and used as a template for PCR.

A 1.0-µl portion of the anchor-ligated cDNA dilution was subjected to PCR for amplification using the primers AP-2 and H11-E, as follows.

Said portion was kept at 82° C. for 1 minute, the primers were then added, and 35 PCR cycles were conducted (each cycle comprising keeping at 92° C. for 0.5 minute, at 56° C. for 0.5 minute and at 72° C. for 1.0 minute), followed by 15 minutes of incubation at 72° C. The PCR products were cloned into the pBluescript SK(–) vector at the EcoRV site thereof. The desired transformants were selected by colony hybridization using $^{32}$P-ATP end-labeled oligo H11-I. The positive colonies were subjected to sequence determination by the dideoxy termination method [Sanger et al., Proc. Natl. Acad. Sci., U.S.A., 74, 5463–5467 (1977)].

The thus-obtained cDNA, which is a gene of the present invention is hereinafter referred to as "OTK7".
(3) Northern hybridization The expression of the gene OTK7 of the present invention was examined in various tissues using a human multiple tissue Northern blot system (Clontech).

Thus, blots were subjected to 4 hours of pre-hybridization at 50° C. in a solution comprising 50% formamide, 10×Denhardt's solution, 5×SSPE, 2% SDS and 100 μg/ml of denatured salmon sperm DNA, with [³²P]-labeled cDNA as a probe, followed by 18 hours of hybridization. The blots were washed, at room temperature, three times with 2×SSC/0.05% SDS over 10 minutes and then two times with 0.1×SSC/0.1% SDS over 15 minutes, and subjected to autoradiography at −80° C. for 16 hours.

(4) Chromosome mapping

Chromosome mapping was performed in the manner of direct R-banding fluorescence in situ hybridization [FISH; Takahashi et al., Hum. Genet., 86, 14–16 (1990) and ibid., 88, 119–121 (1991)].

(5) Results a) DNA sequence of OTK7 gene and corresponding amino acid sequence

The nucleotide sequence of the OTK7 cDNA and the corresponding amino acid sequence are shown under SEQ ID NO:3.

Referring to SEQ ID NO:3, the sequence consisting of the 1289th to 1291st bases is the termination codon (TAA), the sequence comprising the 317th to 1096th bases corresponds to the zinc finger domains, the sequence from the 20th to 22nd bases (ATG) is the initiation methionine codon, and the 1363rd to 1368th bases (ATTAAA) constitute a polyadenylation signal.

The OTK7 cDNA comprises a total of 1399 bases, inclusive of a 1269-base open reading frame coding for 423 amino acid residues.

As far as the 5' three fourths of its coding region is concerned, said cDNA showed 63% homology in nucleotides and 58% homology in amino acids to Xenopus TFIIIA.

Such hTFIIIA has nine zinc finger domains and the amino acid sequences thereof well conserve the $C_2H_2$ finger domains of Xenopus TFIIIA except for the 6th finger domain which has only 3 amino acid residues between two cysteine residues instead of 5 amino acid residues in the case of Xenopus TFIIIA.

In the C terminal region, the homology between the two is not so high. They differ also in the size of N terminal region. Whereas, in Xenopus TFIIIA, there are 14 amino acid residues upstream of the first finger domain, there are 99 amino acid residues in hTFIIIA. This N terminal region of hTFIIIA shows no homology to any of the so-far known gene products.

The homology of hTFIIIA to other known DNA binding proteins is limited to a relatively small region, as follows:

Upon comparison of 289 amino acids, hTFIIIA showed 37% homology to Xenopus 5S RNA binding protein p43 (Joho et al, Cell, 61:293–300 (1990));

Upon comparison of 126 amino acids, hTFIIIA showed 35% homology to human Wilms tumor gene product WT1 (Gessler et al, Nature, 343:774–778 (1990);

Upon comparison of 95 amino acids, hTFIIIA showed 40% homology to human transcriptional repressor YYA (Shi et al, Cell, 67:377–388 (1991));

Upon comparison of 91 amino acids, hTFIIIA showed 44% homology to human GT box binding protein (Kingsley et al, Mol. Cell. Biol., 12:4251–4261 (1992));

Upon comparison of 152 amino acids, hTFIIIA showed 37% homology to human myc-associated zinc finger protein (Bossone et al, Proc. Natl. Acad. Sci, U.S.A., 89:7452–7456 (1992)).

b) Northern blot analysis

Figure 1:
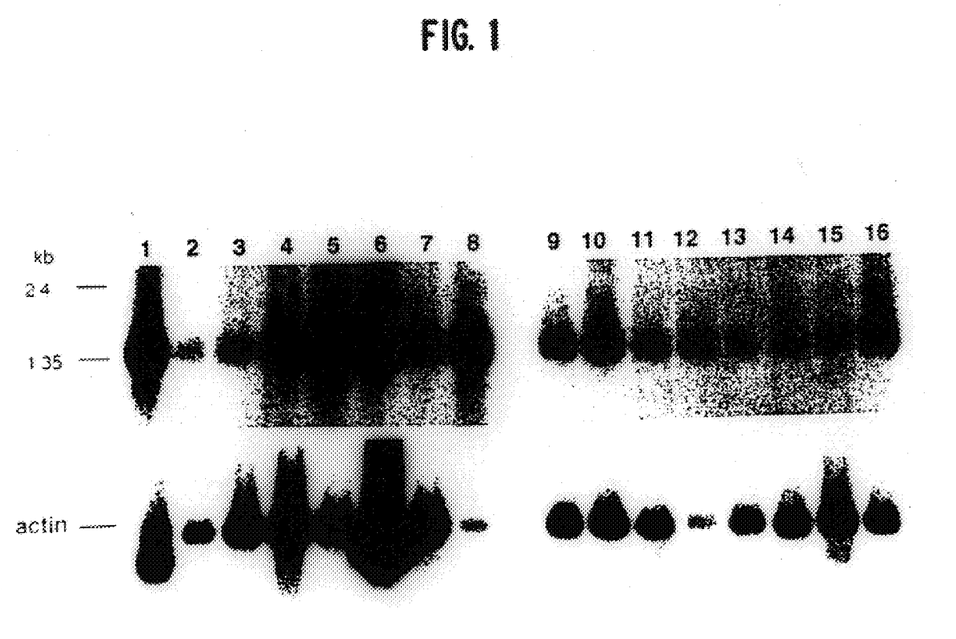
FIG. 1 shows the results of Northern blotting for visualizing the expression of the gene of the present invention in various tissues.

The levels of expression of hTFIIIA in various tissues are shown in FIG. 1.

In FIG. 1, the results of the above-mentioned test (hTFIIIA expression) with a 1.1 kbp cDNA as a probe are shown in the upper row, and the results (controls) of a β-actin m-RNA detection test conducted for the same blots in the same manner using a β-actin probe are shown in the lower row. The lanes are respectively for the following:

Lane 1: heart
Lane 2: brain
Lane 3: placenta
Lane 4: lung
Lane 5: liver
Lane 6: skeletal muscle
Lane 7: kidney
Lane 8: pancreas
Lane 9: spleen
Lane 10: thymus
Lane 11: prostate
Lane 12: testis
Lane 13: ovary
Lane 14: small intestine
Lane 15: colon
Lane 16: peripheral blood leukocyte The size of the hTFIIIA transcript was estimated at about 1400 bp upon Northern analysis. This size is almost in agreement with that of the OTK7 cDNA and, therefore, said cDNA presumably covers approximately the whole sequence of the hTFIIIA mRNA.

While this gene is ubiquitously expressed in all the human tissues tested, the level of expression seems higher in such tissues as pancreas, spleen and peripheral blood leukocyte than in other tissues.

c) Mapping

The hTFIIIA gene was found to reside on the chromosome 13q12.3–13.1.

We claim:

1. An isolated human transcription factor IIIA gene coding for the amino acid sequence of SEQ ID NO:1.

2. The isolated human transcription factor IIIA gene claimed in claim 1, wherein said gene has the nucleotide sequence of SEQ ID NO:2.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 1269 base pairs
        ( B ) TYPE: nucleic acid (C) STRANDEDNESS: single
(D) TOPOLOGY: linear (i i) MOLECULE TYPE: cDNA (x i) SEQUENCE DESCRIPTION: SEQ ID NO:1:

| | | | | | |
|---|---|---|---|---|---|
| ATGCGCAGCA | GCGGCGCCGA | CGCGGGGCGG | TGCCTGGTGA | CCGCGCGCGC | TCCCGGAAGT | 60 |
| GTGCCGGCGT | CGCGCGAAGG | TTCAGCAGGG | AGCCGTGGGC | CGGGCGCGCG | GTTCCCGGCA | 120 |
| CGTGTCTCGG | CACGTGGCAG | CGCGCCTGGC | CCTGGGCTTG | GAGGCGCCGG | CGCCCTGGAT | 180 |
| CCGCCGGCCG | TGGTCGCCGA | GTCGGTGTCG | TCCTTGACCA | TCGCCGACGC | GTTCATTGCA | 240 |
| GCCGGCGAGA | GCTCAGCTCC | GACCCCGCCG | CGCCCCGCGC | TTCCCAGGAG | GTTCATCTGC | 300 |
| TCCTTCCCTG | ACTGCAGCGC | CAATTACAGC | AAAGCCTGGA | AGCTTGACGC | GCACCTGTGC | 360 |
| AAGCACACGG | GGGAGAGACC | ATTTGTTTGT | GACTATGAAG | GGTGTGGCAA | GGCCTTCATC | 420 |
| AGGGACTACC | ATCTGAGCCG | CCACATTCTG | ACTCACACAG | GAGAAAAGCC | GTTTGTTTGT | 480 |
| GCAGCCAATG | GCTGTGATCA | AAAATTCAAC | ACAAAATCAA | ACTTGAAGAA | ACATTTTGAA | 540 |
| CGCAAACATG | AAAATCAACA | AAAACAATAT | ATATGCAGTT | TTGAAGACTG | TAAGAAGACC | 600 |
| TTTAAGAAAC | ATCAGCAGAT | GAAAATCCAT | CAGTGCCAGA | ATACCAATGA | ACCTCTATTC | 660 |
| AAGTGTACCC | AGGAAGGATG | TGGGAAACAC | TTTGCATCAC | CCAGCAAGCT | GAAACGACAT | 720 |
| GCCAAGGCCC | ACGAGGGCTA | TGTATGTCAA | AAAGGATGTT | CCTTTGTGGC | AAAAACATGG | 780 |
| ACGGAACTTC | TGAAACATGT | GAGAGAAACC | CATAAGAGG | AAATACTATG | TGAAGTATGC | 840 |
| CGGAAAACAT | TTAAACGCAA | AGATTACCTT | AAGCAACACA | TGAAAACTCA | TGCCCCAGAA | 900 |
| AGGGATGTAT | GTCGCTGTCC | AAGAGAAGGC | TGTGGAAGAA | CCTATACAAC | TGTGTTTAAT | 960 |
| CTCCAAAGCC | ATATCCTCTC | CTTCCATGAG | GAAAGCCGCC | CTTTTGTGTG | TGAACATGCT | 1020 |
| GGCTGTGGCA | AAACATTTGC | AATGAAACAA | AGTCTCACTA | GGCATGCTGT | TGTACATGAT | 1080 |
| CCTGACAAGA | AGAAAATGAA | GCTCAAAGTC | AAAAAATCTC | GTGAAAACG | GGAGTTTGGC | 1140 |
| CTCTCATCTC | AGTGGATATA | TCCTCCCAAA | AGGAAACAAG | GGCAAGGCTT | ATCTTTGTGT | 1200 |
| CAAAACGGAG | AGTCACCCAA | CTGTGTGGAA | GACAAGATGC | TCTCGACAGT | TGCAGTACTT | 1260 |
| ACCCTTGGC | | | | | | 1269 |

(2) INFORMATION FOR SEQ ID NO:2:

(i) SEQUENCE CHARACTERISTICS:
        (A) LENGTH: 1399 base pairs
        (B) TYPE: nucleic acid
        (C) STRANDEDNESS: single
        (D) TOPOLOGY: linear     (i i) MOLECULE TYPE: cDNA     (v i i) IMMEDIATE SOURCE:
        (A) LIBRARY: human fetal brain cDNA
        (B) CLONE: OTK7

(i x) FEATURE:
        (A) NAME/KEY: CDS
        (B) LOCATION: 20..1288
        (C) IDENTIFICATION METHOD: S     (x i) SEQUENCE DESCRIPTION: SEQ ID NO:2:

```
ATGCGCGATC TCCCGGAGC ATG CGC AGC AGC GGC GCC GAC GCG GGG CGG TGC        52
                    Met Arg Ser Ser Gly Ala Asp Ala Gly Arg Cys
                     1               5                  10

CTG GTG ACC GCG CGC GCT CCC GGA AGT GTG CCG GCG TCG CGC GAA GGT         100
Leu Val Thr Ala Arg Ala Pro Gly Ser Val Pro Ala Ser Arg Glu Gly
 15                  20                  25
```

-continued

| | | | | | | | | | | | | | | | | |
|---|---|---|---|---|---|---|---|---|---|---|---|---|---|---|---|---|
| TCA | GCA | GGG | AGC | CGT | GGG | CCG | GGC | GCG | CGG | TTC | CCG | GCA | CGT | GTC | TCG | 148 |
| Ser | Ala | Gly | Ser | Arg | Gly | Pro | Gly | Ala | Arg | Phe | Pro | Ala | Arg | Val | Ser | |
| | | 30 | | | 35 | | | | | | | 40 | | | | |
| GCA | CGT | GGC | AGC | GCG | CCT | GGC | CCT | GGG | CTT | GGA | GGC | GCC | GGC | GCC | CTG | 196 |
| Ala | Arg | Gly | Ser | Ala | Pro | Gly | Pro | Gly | Leu | Gly | Gly | Ala | Gly | Ala | Leu | |
| | 45 | | | | | 50 | | | | | 55 | | | | | |
| GAT | CCG | CCG | GCC | GTG | GTC | GCC | GAG | TCG | GTG | TCG | TCC | TTG | ACC | ATC | GCC | 244 |
| Asp | Pro | Pro | Ala | Val | Val | Ala | Glu | Ser | Val | Ser | Ser | Leu | Thr | Ile | Ala | |
| 60 | | | | | 65 | | | | | 70 | | | | | 75 | |
| GAC | GCG | TTC | ATT | GCA | GCC | GGC | GAG | AGC | TCA | GCT | CCG | ACC | CCG | CCG | CGC | 292 |
| Asp | Ala | Phe | Ile | Ala | Ala | Gly | Glu | Ser | Ser | Ala | Pro | Thr | Pro | Pro | Arg | |
| | | | | 80 | | | | | 85 | | | | | 90 | | |
| CCC | GCG | CTT | CCC | AGG | AGG | TTC | ATC | TGC | TCC | TTC | CCT | GAC | TGC | AGC | GCC | 340 |
| Pro | Ala | Leu | Pro | Arg | Arg | Phe | Ile | Cys | Ser | Phe | Pro | Asp | Cys | Ser | Ala | |
| | | | 95 | | | | | 100 | | | | | 105 | | | |
| AAT | TAC | AGC | AAA | GCC | TGG | AAG | CTT | GAC | GCG | CAC | CTG | TGC | AAG | CAC | ACG | 388 |
| Asn | Tyr | Ser | Lys | Ala | Trp | Lys | Leu | Asp | Ala | His | Leu | Cys | Lys | His | Thr | |
| | | 110 | | | | | 115 | | | | | 120 | | | | |
| GGG | GAG | AGA | CCA | TTT | GTT | TGT | GAC | TAT | GAA | GGG | TGT | GGC | AAG | GCC | TTC | 436 |
| Gly | Glu | Arg | Pro | Phe | Val | Cys | Asp | Tyr | Glu | Gly | Cys | Gly | Lys | Ala | Phe | |
| | 125 | | | | | 130 | | | | | 135 | | | | | |
| ATC | AGG | GAC | TAC | CAT | CTG | AGC | CGC | CAC | ATT | CTG | ACT | CAC | ACA | GGA | GAA | 484 |
| Ile | Arg | Asp | Tyr | His | Leu | Ser | Arg | His | Ile | Leu | Thr | His | Thr | Gly | Glu | |
| 140 | | | | | 145 | | | | | 150 | | | | | 155 | |
| AAG | CCG | TTT | GTT | TGT | GCA | GCC | AAT | GGC | TGT | GAT | CAA | AAA | TTC | AAC | ACA | 532 |
| Lys | Pro | Phe | Val | Cys | Ala | Ala | Asn | Gly | Cys | Asp | Gln | Lys | Phe | Asn | Thr | |
| | | | | 160 | | | | | 165 | | | | | 170 | | |
| AAA | TCA | AAC | TTG | AAG | AAA | CAT | TTT | GAA | CGC | AAA | CAT | GAA | AAT | CAA | CAA | 580 |
| Lys | Ser | Asn | Leu | Lys | Lys | His | Phe | Glu | Arg | Lys | His | Glu | Asn | Gln | Gln | |
| | | | 175 | | | | | 180 | | | | | 185 | | | |
| AAA | CAA | TAT | ATA | TGC | AGT | TTT | GAA | GAC | TGT | AAG | AAG | ACC | TTT | AAG | AAA | 628 |
| Lys | Gln | Tyr | Ile | Cys | Ser | Phe | Glu | Asp | Cys | Lys | Lys | Thr | Phe | Lys | Lys | |
| | | 190 | | | | | 195 | | | | | 200 | | | | |
| CAT | CAG | CAG | ATG | AAA | ATC | CAT | CAG | TGC | CAG | AAT | ACC | AAT | GAA | CCT | CTA | 676 |
| His | Gln | Gln | Met | Lys | Ile | His | Gln | Cys | Gln | Asn | Thr | Asn | Glu | Pro | Leu | |
| | 205 | | | | | 210 | | | | | 215 | | | | | |
| TTC | AAG | TGT | ACC | CAG | GAA | GGA | TGT | GGG | AAA | CAC | TTT | GCA | TCA | CCC | AGC | 724 |
| Phe | Lys | Cys | Thr | Gln | Glu | Gly | Cys | Gly | Lys | His | Phe | Ala | Ser | Pro | Ser | |
| 220 | | | | | 225 | | | | | 230 | | | | | 235 | |
| AAG | CTG | AAA | CGA | CAT | GCC | AAG | GCC | CAC | GAG | GGC | TAT | GTA | TGT | CAA | AAA | 772 |
| Lys | Leu | Lys | Arg | His | Ala | Lys | Ala | His | Glu | Gly | Tyr | Val | Cys | Gln | Lys | |
| | | | | 240 | | | | | 245 | | | | | 250 | | |
| GGA | TGT | TCC | TTT | GTG | GCA | AAA | ACA | TGG | ACG | GAA | CTT | CTG | AAA | CAT | GTG | 820 |
| Gly | Cys | Ser | Phe | Val | Ala | Lys | Thr | Trp | Thr | Glu | Leu | Leu | Lys | His | Val | |
| | | | 255 | | | | | 260 | | | | | 265 | | | |
| AGA | GAA | ACC | CAT | AAA | GAG | GAA | ATA | CTA | TGT | GAA | GTA | TGC | CGG | AAA | ACA | 868 |
| Arg | Glu | Thr | His | Lys | Glu | Glu | Ile | Leu | Cys | Glu | Val | Cys | Arg | Lys | Thr | |
| | | 270 | | | | | 275 | | | | | 280 | | | | |
| TTT | AAA | CGC | AAA | GAT | TAC | CTT | AAG | CAA | CAC | ATG | AAA | ACT | CAT | GCC | CCA | 916 |
| Phe | Lys | Arg | Lys | Asp | Tyr | Leu | Lys | Gln | His | Met | Lys | Thr | His | Ala | Pro | |
| | 285 | | | | | 290 | | | | | 295 | | | | | |
| GAA | AGG | GAT | GTA | TGT | CGC | TGT | CCA | AGA | GAA | GGC | TGT | GGA | AGA | ACC | TAT | 964 |
| Glu | Arg | Asp | Val | Cys | Arg | Cys | Pro | Arg | Glu | Gly | Cys | Gly | Arg | Thr | Tyr | |
| 300 | | | | | 305 | | | | | 310 | | | | | 315 | |
| ACA | ACT | GTG | TTT | AAT | CTC | CAA | AGC | CAT | ATC | CTC | TCC | TTC | CAT | GAG | GAA | 1012 |
| Thr | Thr | Val | Phe | Asn | Leu | Gln | Ser | His | Ile | Leu | Ser | Phe | His | Glu | Glu | |
| | | | | 320 | | | | | 325 | | | | | 330 | | |
| AGC | CGC | CCT | TTT | GTG | TGT | GAA | CAT | GCT | GGC | TGT | GGA | AAA | ACA | TTT | GCA | 1060 |
| Ser | Arg | Pro | Phe | Val | Cys | Glu | His | Ala | Gly | Cys | Gly | Lys | Thr | Phe | Ala | |
| | | | 335 | | | | | 340 | | | | | 345 | | | |

| | | | | | | | | | | | | | | | | |
|---|---|---|---|---|---|---|---|---|---|---|---|---|---|---|---|---|
| ATG | AAA | CAA | AGT | CTC | ACT | AGG | CAT | GCT | GTT | GTA | CAT | GAT | CCT | GAC | AAG | 1108 |
| Met | Lys | Gln | Ser | Leu | Thr | Arg | His | Ala | Val | Val | His | Asp | Pro | Asp | Lys | |
| | | 350 | | | | | 355 | | | | | 360 | | | | |
| AAG | AAA | ATG | AAG | CTC | AAA | GTC | AAA | AAA | TCT | CGT | GAA | AAA | CGG | GAG | TTT | 1156 |
| Lys | Lys | Met | Lys | Leu | Lys | Val | Lys | Lys | Ser | Arg | Glu | Lys | Arg | Glu | Phe | |
| | | 365 | | | | 370 | | | | | 375 | | | | | |
| GGC | CTC | TCA | TCT | CAG | TGG | ATA | TAT | CCT | CCC | AAA | AGG | AAA | CAA | GGG | CAA | 1204 |
| Gly | Leu | Ser | Ser | Gln | Trp | Ile | Tyr | Pro | Pro | Lys | Arg | Lys | Gln | Gly | Gln | |
| 380 | | | | | 385 | | | | | 390 | | | | | 395 | |
| GGC | TTA | TCT | TTG | TGT | CAA | AAC | GGA | GAG | TCA | CCC | AAC | TGT | GTG | GAA | GAC | 1252 |
| Gly | Leu | Ser | Leu | Cys | Gln | Asn | Gly | Glu | Ser | Pro | Asn | Cys | Val | Glu | Asp | |
| | | | | 400 | | | | | 405 | | | | | 410 | | |
| AAG | ATG | CTC | TCG | ACA | GTT | GCA | GTA | CTT | ACC | CTT | GGC | TAAGAACTGC | | | | 1298 |
| Lys | Met | Leu | Ser | Thr | Val | Ala | Val | Leu | Thr | Leu | Gly | | | | | |
| | | | 415 | | | | | 420 | | | | | | | | |

ACTGCTTTGT TTAAAGGACT GCAGACCAAG GAGTCGAGCT TTCTCTCAGA GCATGCTTTT   1358

CTTTATTAAA ATTACTGATG CAGAAAAAAA AAAAAAAAA A                       1399

( 2 ) INFORMATION FOR SEQ ID NO:3:

( i ) SEQUENCE CHARACTERISTICS:
        ( A ) LENGTH: 423 amino acids
        ( B ) TYPE: amino acid
        ( D ) TOPOLOGY: linear     ( i i ) MOLECULE TYPE: protein     ( x i ) SEQUENCE DESCRIPTION: SEQ ID NO:3:

| | | | | | | | | | | | | | | |
|---|---|---|---|---|---|---|---|---|---|---|---|---|---|---|
| Met | Arg | Ser | Ser | Gly | Ala | Asp | Ala | Gly | Arg | Cys | Leu | Val | Thr | Ala | Arg |
| 1 | | | | 5 | | | | | 10 | | | | | 15 | |
| Ala | Pro | Gly | Ser | Val | Pro | Ala | Ser | Arg | Glu | Gly | Ser | Ala | Gly | Ser | Arg |
| | | | 20 | | | | | 25 | | | | | 30 | | |
| Gly | Pro | Gly | Ala | Arg | Phe | Pro | Ala | Arg | Val | Ser | Ala | Arg | Gly | Ser | Ala |
| | | | | 35 | | | | | 40 | | | | | 45 | |
| Pro | Gly | Pro | Gly | Leu | Gly | Gly | Ala | Gly | Ala | Leu | Asp | Pro | Pro | Ala | Val |
| | 50 | | | | | 55 | | | | | 60 | | | | |
| Val | Ala | Glu | Ser | Val | Ser | Ser | Leu | Thr | Ile | Ala | Asp | Ala | Phe | Ile | Ala |
| 65 | | | | | 70 | | | | | 75 | | | | | 80 |
| Ala | Gly | Glu | Ser | Ser | Ala | Pro | Thr | Pro | Pro | Arg | Pro | Ala | Leu | Pro | Arg |
| | | | | 85 | | | | | 90 | | | | | 95 | |
| Arg | Phe | Ile | Cys | Ser | Phe | Pro | Asp | Cys | Ser | Ala | Asn | Tyr | Ser | Lys | Ala |
| | | | | 100 | | | | | 105 | | | | | 110 | |
| Trp | Lys | Leu | Asp | Ala | His | Leu | Cys | Lys | His | Thr | Gly | Glu | Arg | Pro | Phe |
| | | | 115 | | | | | 120 | | | | | 125 | | |
| Val | Cys | Asp | Tyr | Glu | Gly | Cys | Gly | Lys | Ala | Phe | Ile | Arg | Asp | Tyr | His |
| | 130 | | | | | 135 | | | | | 140 | | | | |
| Leu | Ser | Arg | His | Ile | Leu | Thr | His | Thr | Gly | Glu | Lys | Pro | Phe | Val | Cys |
| 145 | | | | | 150 | | | | | 155 | | | | | 160 |
| Ala | Ala | Asn | Gly | Cys | Asp | Gln | Lys | Phe | Asn | Thr | Lys | Ser | Asn | Leu | Lys |
| | | | | 165 | | | | | 170 | | | | | 175 | |
| Lys | His | Phe | Glu | Arg | Lys | His | Glu | Asn | Gln | Gln | Lys | Gln | Tyr | Ile | Cys |
| | | | | 180 | | | | | 185 | | | | | 190 | |
| Ser | Phe | Glu | Asp | Cys | Lys | Lys | Thr | Phe | Lys | Lys | His | Gln | Gln | Met | Lys |
| | | | 195 | | | | | 200 | | | | | 205 | | |
| Ile | His | Gln | Cys | Gln | Asn | Thr | Asn | Glu | Pro | Leu | Phe | Lys | Cys | Thr | Gln |
| | 210 | | | | | 215 | | | | | 220 | | | | |

-continued

| | | | | | | | | | | | | | | |
|---|---|---|---|---|---|---|---|---|---|---|---|---|---|---|
| Glu 225 | Gly | Cys | Gly | Lys | His 230 | Phe | Ala | Ser | Pro | Ser 235 | Lys | Leu | Lys | Arg | His 240 |
| Ala | Lys | Ala | His | Glu 245 | Gly | Tyr | Val | Cys | Gln 250 | Lys | Gly | Cys | Ser | Phe 255 | Val |
| Ala | Lys | Thr | Trp 260 | Thr | Glu | Leu | Leu | Lys | His 265 | Val | Arg | Glu | Thr 270 | His | Lys |
| Glu | Glu | Ile 275 | Leu | Cys | Glu | Val | Cys 280 | Arg | Lys | Thr | Phe | Lys 285 | Arg | Lys | Asp |
| Tyr | Leu 290 | Lys | Gln | His | Met | Lys 295 | Thr | His | Ala | Pro | Glu 300 | Arg | Asp | Val | Cys |
| Arg 305 | Cys | Pro | Arg | Glu | Gly 310 | Cys | Gly | Arg | Thr | Tyr 315 | Thr | Thr | Val | Phe | Asn 320 |
| Leu | Gln | Ser | His | Ile 325 | Leu | Ser | Phe | His | Glu 330 | Glu | Ser | Arg | Pro | Phe 335 | Val |
| Cys | Glu | His | Ala 340 | Gly | Cys | Gly | Lys | Thr 345 | Phe | Ala | Met | Lys | Gln 350 | Ser | Leu |
| Thr | Arg | His 355 | Ala | Val | Val | His | Asp 360 | Pro | Asp | Lys | Lys | Lys 365 | Met | Lys | Leu |
| Lys | Val 370 | Lys | Lys | Ser | Arg | Glu 375 | Lys | Arg | Glu | Phe | Gly 380 | Leu | Ser | Ser | Gln |
| Trp 385 | Ile | Tyr | Pro | Pro | Lys 390 | Arg | Lys | Gln | Gly | Gln 395 | Gly | Leu | Ser | Leu | Cys 400 |
| Gln | Asn | Gly | Glu | Ser 405 | Pro | Asn | Cys | Val | Glu 410 | Asp | Lys | Met | Leu | Ser 415 | Thr |
| Val | Ala | Val | Leu | Thr 420 | Leu | Gly | | | | | | | | | |

( 2 ) INFORMATION FOR SEQ ID NO:4:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear     ( i i ) MOLECULE TYPE: cDNA     ( x i ) SEQUENCE DESCRIPTION: SEQ ID NO:4:

ATGGTCAAGG ACGACA 16

( 2 ) INFORMATION FOR SEQ ID NO:5:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear     ( i i ) MOLECULE TYPE: cDNA     ( x i ) SEQUENCE DESCRIPTION: SEQ ID NO:5:

AATGAATTCA TAAGGACGAC ACCGACT 27

( 2 ) INFORMATION FOR SEQ ID NO:6:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear     ( i i ) MOLECULE TYPE: cDNA ( x i ) SEQUENCE DESCRIPTION: SEQ ID NO:6:

CCTCCAAGCC CAGGGCCA 18

( 2 ) INFORMATION FOR SEQ ID NO:7:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear     ( i i ) MOLECULE TYPE: cDNA     ( x i ) SEQUENCE DESCRIPTION: SEQ ID NO:7:

CAGAATCGAT AGTGAATTCG TG 22

( 2 ) INFORMATION FOR SEQ ID NO:8:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear     ( i i ) MOLECULE TYPE: cDNA     ( x i ) SEQUENCE DESCRIPTION: SEQ ID NO:8:

CACGAATTCA CTATCGATTC TGGAACCTTC AGACC 35